(12) United States Patent
McKenna

(10) Patent No.: US 8,553,223 B2
(45) Date of Patent: Oct. 8, 2013

(54) BIODEGRADABLE FIBERS FOR SENSING

(75) Inventor: Edward McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 657 days.

(21) Appl. No.: 12/751,797

(22) Filed: Mar. 31, 2010

(65) Prior Publication Data

US 2011/0242532 A1 Oct. 6, 2011

(51) Int. Cl.
*G01J 3/42* (2006.01)

(52) U.S. Cl.
USPC .......................................................... 356/319

(58) Field of Classification Search
USPC .................................................. 356/319–325
See application file for complete search history.

(56) References Cited

U.S. PATENT DOCUMENTS

| | | | |
|---|---|---|---|
| 3,721,813 A | 3/1973 | Condon et al. |
| 4,971,062 A | 11/1990 | Hasebe et al. |
| 4,974,591 A | 12/1990 | Awazu et al. |
| 5,028,787 A | 7/1991 | Rosenthal et al. |
| 5,035,243 A | 7/1991 | Muz |
| 5,065,749 A | 11/1991 | Hasebe et al. |
| 5,084,327 A | 1/1992 | Stengel |
| 5,088,493 A | 2/1992 | Giannini et al. |
| 5,094,240 A | 3/1992 | Muz |
| 5,275,159 A | 1/1994 | Griebel |
| 5,279,295 A | 1/1994 | Martens et al. |
| 5,348,003 A | 9/1994 | Caro |
| 5,429,129 A | 7/1995 | Lovejoy et al. |
| 5,474,065 A | 12/1995 | Meathrel et al. |
| 5,483,646 A | 1/1996 | Uchikoga |
| 5,494,032 A | 2/1996 | Robinson et al. |
| 5,511,546 A | 4/1996 | Hon |
| 5,551,424 A | 9/1996 | Morrison et al. |
| 5,619,992 A | 4/1997 | Guthrie et al. |
| 5,666,952 A | 9/1997 | Fuse et al. |
| D393,830 S | 4/1998 | Tobler et al. |
| 5,779,631 A | 7/1998 | Chance |
| 5,871,442 A | 2/1999 | Madarasz et al. |
| 6,014,576 A | 1/2000 | Raley |
| 6,064,899 A | 5/2000 | Fein et al. |
| 6,081,742 A | 6/2000 | Amano et al. |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Burkart, Karl. "Boy discovers microbe that eats plastic". Jun. 12, 2009.*

(Continued)

*Primary Examiner* — Tara S Pajoohi Gomez

(74) *Attorney, Agent, or Firm* — Fletcher Yoder, P.C.

(57) ABSTRACT

Biodegradable waveguides and their uses with devices, such as medical devices, are described. In one embodiment, an optically transmissive fibrous structure comprising biodegradable fiber waveguides may be disposed on a surface of a bandage. The bandage in combination with the optically transmissive fibrous structure may allow for simultaneously monitoring and covering an injured area of a patient. In one embodiment, the fiber waveguides may be provided as multi-channel/multi-core biodegradable fiber waveguides for transmitting light to and from a patient tissue. In some implementations, the bandage may include hydrogel-based biodegradable fiber waveguides that may deliver therapeutics to an injured patient area.

20 Claims, 7 Drawing Sheets

(56) References Cited

U.S. PATENT DOCUMENTS

| | | | |
|---|---|---|---|
| 6,095,974 | A | 8/2000 | Shemwell et al. |
| 6,144,444 | A | 11/2000 | Haworth et al. |
| 6,253,097 | B1 | 6/2001 | Aronow et al. |
| 6,261,236 | B1 | 7/2001 | Grimblatov |
| 6,285,895 | B1 | 9/2001 | Ristolainen et al. |
| 6,353,750 | B1 | 3/2002 | Kimura et al. |
| 6,419,671 | B1 | 7/2002 | Lemberg |
| 6,461,305 | B1 | 10/2002 | Schnall |
| 6,512,937 | B2 | 1/2003 | Blank et al. |
| 6,564,088 | B1 | 5/2003 | Soller et al. |
| 6,589,172 | B2 | 7/2003 | Williams et al. |
| 6,591,122 | B2 | 7/2003 | Schmitt |
| 6,719,686 | B2 | 4/2004 | Coakley et al. |
| 6,791,689 | B1 | 9/2004 | Weckström |
| 6,793,654 | B2 | 9/2004 | Lemberg |
| 6,839,496 | B1 | 1/2005 | Mills et al. |
| 6,859,658 | B1 | 2/2005 | Krug |
| 6,916,289 | B2 | 7/2005 | Schnall |
| 6,971,580 | B2 | 12/2005 | Zhu et al. |
| 6,992,751 | B2 | 1/2006 | Okita et al. |
| 7,035,489 | B2 | 4/2006 | Glebov et al. |
| 7,047,054 | B2 | 5/2006 | Benni |
| 7,198,778 | B2 | 4/2007 | Achilefu et al. |
| 7,236,811 | B2 | 6/2007 | Schmitt |
| 7,236,881 | B2 | 6/2007 | Liu et al. |
| 7,313,427 | B2 | 12/2007 | Benni |
| 7,319,894 | B2 | 1/2008 | Higgins |
| 7,387,607 | B2 | 6/2008 | Holt et al. |
| 7,426,407 | B2 | 9/2008 | Higgins |
| 7,469,158 | B2 | 12/2008 | Cutler et al. |
| 7,572,229 | B2 | 8/2009 | Yeo et al. |
| 7,574,244 | B2 | 8/2009 | Eghbal et al. |
| 7,702,374 | B2 | 4/2010 | Ishizuka et al. |
| 2004/0098009 | A1 | 5/2004 | Boecker et al. |
| 2005/0075550 | A1 | 4/2005 | Lindekugel |
| 2005/0113656 | A1 | 5/2005 | Chance |
| 2005/0177034 | A1 | 8/2005 | Beaumont |
| 2005/0197548 | A1 | 9/2005 | Dietiker |
| 2005/0228253 | A1 | 10/2005 | Debreczeny |
| 2006/0106293 | A1 | 5/2006 | Fantini |
| 2006/0247501 | A1 | 11/2006 | Ali |
| 2007/0073121 | A1 | 3/2007 | Hoarau et al. |
| 2008/0017800 | A1 | 1/2008 | Benni |
| 2008/0108887 | A1 | 5/2008 | Higgins |
| 2008/0262328 | A1 | 10/2008 | Adams |
| 2009/0216097 | A1* | 8/2009 | Wilson et al. .............. 600/327 |
| 2010/0013642 | A1 | 1/2010 | Watson et al. |
| 2010/0016680 | A1 | 1/2010 | Addison et al. |
| 2010/0017142 | A1 | 1/2010 | Watson et al. |
| 2010/0081897 | A1 | 4/2010 | Li et al. |
| 2010/0081899 | A1 | 4/2010 | McKenna |
| 2010/0081901 | A1 | 4/2010 | Buice et al. |
| 2010/0081902 | A1 | 4/2010 | McKenna et al. |
| 2010/0081912 | A1 | 4/2010 | McKenna et al. |
| 2010/0081940 | A1 | 4/2010 | McKenna |
| 2010/0081960 | A1 | 4/2010 | McKenna |
| 2011/0071366 | A1 | 3/2011 | McKenna |
| 2011/0071376 | A1 | 3/2011 | McKenna |
| 2011/0071378 | A1 | 3/2011 | McKenna et al. |
| 2011/0071598 | A1 | 3/2011 | McKenna |
| 2011/0190612 | A1 | 8/2011 | McKenna et al. |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| EP | 702931 | 3/1996 |
| EP | 1579800 | 9/2005 |
| EP | 1852101 | 11/2007 |
| FR | 2685865 | 7/1993 |
| JP | 3245042 | 10/1991 |
| JP | 6014906 | 1/1994 |
| JP | 24261364 | 9/2004 |
| JP | 3635331 | 4/2005 |
| JP | 26297125 | 11/2006 |
| JP | 28119026 | 5/2008 |
| WO | WO9309711 | 5/1993 |
| WO | WO9502358 | 1/1995 |
| WO | WO9736536 | 10/1997 |
| WO | WO03077750 | 9/2003 |
| WO | WO2005010567 | 2/2005 |

OTHER PUBLICATIONS

Bentley, David J. et al.; "Measure Pressure with Thin Film"; Paper Film & Foil Converter; May 1, 2003.

Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.

Dekock, Marc; "Pulse Oximetry Probe Adhesive Disks: a Potential for Infant Aspiration," Anesthesiology, vol. 89, pp. 1603-1604 (1998).

Ding, L., et al., Large Refractive Index Change in Silicone-Based and Non-Silicone-Based Hydrogel Polymers Induced by Femtosecond Laser Micro-Machining, Optics Express, Nov. 27, 2006, vol. 14, No. 24.

Ding,L., et al., Femtosecond Laser Micromachining of Waveguides in Silicone-Based Hydrogel Polymers, Applied Optics, Jun. 2, 2008, vol. 47, No. 17, pp. 3100-3108.

Dupuis, A., et al., Prospective for Biodegradable Microstructure Optical Fibers, Optics Letters, Jan. 15, 2007, vol. 32, No. 2, pp. 109-111.

Earthrowl-Gould, T., et al.; "Chest and abdominal surface motion measurement for continuous monitoring of respiratory function," Proc. Instn Mech Engrs, V215, Part H; pp. 515-520 (2001).

Faisst, Karin, et al.; "Intrapartum Reflectance Pulse Oximetry: Effects of Sensor Location and Fixation Duration on Oxygen Saturation Readings," Journal of Clinical Monitoring, vol. 13, pp. 299-302 (1997).

Ferrell, T.L., et al.; "Medical Telesensors," SPIE, vol. 3253, pp. 193-198 (1998).

Gisiger, P.A., et al.; "OxiCarbo®, a single sensor for the non-invasive measurement of arterial oxygen saturation and CO2 partial pressure at the ear lobe," Sensor and Actuators, vol. B-76, pp. 527-530 (2001). http://www.cfw.com.my/fujifilm.html.

Irie, A., et al.; "Respiration Monitors—Pulse Oximeters," Neonatal Care, vol. 15, No. 12, pp. 78-83 (2002) (Article in Japanese—contains English summary of article).

Izumi, Akio, et al.; "Accuracy and Utility of a New Reflectance Pulse Oximeter for Fetal Monitoring During Labor," Journal of Clinical Monitoring, vol. 13, pp. 103-108 (1997).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; pp. 2796.

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Rhee, Sokwoo, et al.; "The Ring Sensor: a New Ambulatory Wearable Sensor for Twenty-Four Hour Patient Monitoring," Proceedings of the 20th annual International Conference of the IEEE Engineering in Medicine and Biology Society, 1998, vol. 20, No. 4, pp. 1906-1919.

Schulz, Christian Eric; "Design of a Pulse Oximetry Sensor Housing Assembly," California State University Master's Thesis, UMI Dissertation Services, UMI No. 1401306, (May 2000) 63 pages.

Shaltis, Phillip, et al.; "Implementation and Validation of a Power-Efficient, High-Speed Modulation Design for Wireless Oxygen Saturation Measurement Systems," IEEE, pp. 193-194 (2002).

"Smaller Product, Tighter Tolerances Pose Dispensing Challenges for Medical Device Manufacturer," Adhesives Age, pp. 40-41 (Oct. 1997).

Urquhart, C., et al.; "Ear probe pulse oximeters and neonates," Anaesthesia, vol. 60, p. 294 (2005).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Yang, Boo-Ho, et al.; "Development of the ring sensor for healthcare automation," Robotics and Autonomous Systems, vol. 30, pp. 273-281 (2000).

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary).

U.S. Appl. No. 12/751,264, filed Mar. 31, 2010, Youzhi Li.
U.S. Appl. No. 12/751,274, filed Mar. 31, 2010, Clark R. Baker, Jr.
U.S. Appl. No. 12/751,785, filed Mar. 31, 2010, Edward M. McKenna.
U.S. Appl. No. 12/751,797, filed Mar. 31, 2010, Edward M. McKenna.
U.S. Appl. No. 12/751,801, filed Mar. 31, 2010, Edward M. McKenna.
U.S. Appl. No. 12/751,806, filed Mar. 31, 2010, Edward M. McKenna.
U.S. Appl. No. 12/771,803, filed Apr. 30, 2010, Edward M. McKenna.
U.S. Appl. No. 12/418,454, filed Apr. 3, 2009, Daniel J. Peters.
U.S. Appl. No. 12/420,148, filed Apr. 8, 2009, Edward M. McKenna.
U.S. Appl. No. 12/420,176, filed Apr. 8, 2009, Youzhi Li.
U.S. Appl. No. 12/434,770, filed May 4, 2009, Youzhi Li.
U.S. Appl. No. 12/538,696, filed Aug. 10, 2009, Dan Lisogurski.
U.S. Appl. No. 12/543,920, filed Aug. 19, 2009, Edward M. McKenna.
U.S. Appl. No. 12/563,848, filed Sep. 21, 2009, Youzhi Li.
U.S. Appl. No. 12/563,852, filed Sep. 21, 2009, Youzhi Li.
U.S. Appl. No. 12/570,394, filed Sep. 30, 2009, Clark R. Baker.
U.S. Appl. No. 12/576,377, filed Oct. 9, 2009, Youzhi Li.
U.S. Appl. No. 12/709,696, filed Feb. 22, 2010, Edward M. McKenna.
U.S. Appl. No. 12/714,531, filed Feb. 28, 2010, Mark C. Miller.
U.S. Appl. No. 12/714,532, filed Feb. 28, 2010, Edward M. McKenna.
U.S. Appl. No. 12/714,533, filed Feb. 28, 2010, Edward M. McKenna.
U.S. Appl. No. 12/714,535, filed Feb. 28, 2010, Edward M. McKenna.
U.S. Appl. No. 12/722,279, filed Mar. 11, 2010, Edward M. McKenna.
U.S. Appl. No. 12/722,355, filed Mar. 11, 2010, David Besko.
U.S. Appl. No. 61/245,571, filed Sep. 24, 2009, Edward M. McKenna.
U.S. Appl. No. 61/245,573, filed Sep. 24, 2009, Edward M. McKenna.
U.S. Appl. No. 61/245,575, filed Sep. 24, 2009, Edward M. McKenna.
U.S. Appl. No. 61/245,580, filed Sep. 24, 2009, Edward M. McKenna.
U.S. Appl. No. 61/300,756, filed Feb. 2, 2010, Edward M. McKenna.

* cited by examiner

BIODEGRADABLE FIBERS FOR SENSING

BACKGROUND

The present disclosure relates generally to medical devices and methods, and more particularly to medical devices that use transmitted light, such as sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present embodiments. Accordingly, it should be understood that these statements are to be read in this light, and not as admissions of prior art.

In medicine it is often useful to monitor various characteristics of patient tissues, such as skin or internal tissues, as part of an early response and/or continuing treatment. For example, it may be desirable to use various techniques to initially measure and continuously monitor one or more physiological characteristics of a patient as part of the treatment process. It may also be desirable to monitor a patient's area of injury for various characteristics, such as characteristics indicative of infection or wound healing. Such techniques may utilize data collected by a sensor, lead, or contact that is typically directly over or in close proximity to the area of injury of the patient. For example, characteristics related to the status or operation of a patient's circulatory, muscular, or neurological systems may be initially measured and continuously monitored using various sensors placed on or within the patient and relayed to some external monitor that can then be assessed. When needed, sensors may be positioned directly on the monitoring site using straps or adhesives and removed afterwards.

Oftentimes, this medical examination may require the removal of a bandage from a sensitive tissue or area of injury. This removal could prove to be detrimental to the health and recovery of a patient with an open wound, where the exposed tissue may be susceptible to infection or blood loss. Additionally, the sensing and assessment of the various characteristics that are monitored may prove to be a difficult task when conventional monitoring equipment is unavailable. Other times, such as during surgery, sensitive and vital tissues may need to be monitored and bandaged simultaneously.

BRIEF DESCRIPTION OF THE DRAWINGS

Advantages of the present embodiments may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to the use of waveguides in medical devices. Such devices may include a sensor, such as for use with a patient monitoring system, having waveguides for transmitting and/or receiving optical signals (e.g., light). The waveguides may be in a variety of forms and may be formed from different materials consistent with any number of desired properties. For example, typical waveguides may include silica and other glass-based fiber optics. As may be appreciated, such materials may not lend themselves to a single-use or to uses in which they may be left in a patient, such as during and/or after a surgical procedure. In contrast, as described within the present disclosure, waveguide materials may be constructed from one or more biodegradable materials such that the waveguides may be integrated into devices and, bandages, wrappings and so forth that are constructed to be left in a patient or to otherwise degrade without additional attention or removal. In one embodiment, the biodegradable waveguides may be optical fibers formed from large fibrous materials, which may have a number of layers and channels for the transmission of light to and from various substrates (e.g., skin). In other embodiments, the waveguides may be formed from a bulk material, such as a hydrogel. In yet another embodiment, the waveguides may be formed from a mixture of large fibrous materials and hydrogels. The integration of biodegradable waveguides into bandages or other structures may provide access to subepidermal tissues that would otherwise be difficult to continuously monitor while simultaneously protecting the monitored area, such as with a bandage. Additionally, a structure utilizing biodegradable waveguides may allow the implantation of sensors into a patient that will degrade away over time and, thus, do not require additional invasive procedures to remove.

Figure 1:
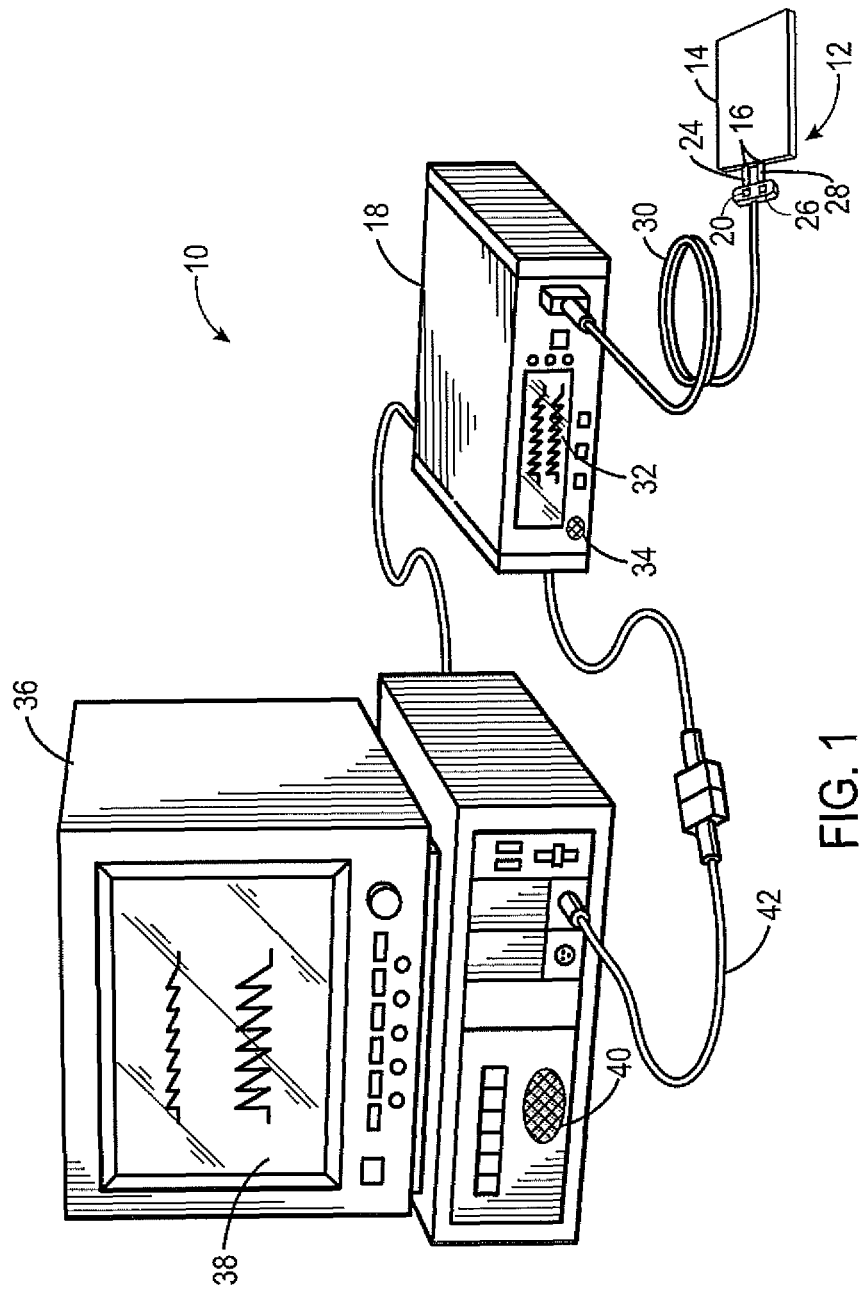
FIG. 1 illustrates a biodegradable fiber sensing system, in accordance with particular aspects of the present disclosure.

With the foregoing comments in mind, biodegradable waveguides as discussed herein may be used in various medical contexts, such as in the placement, on or within a patient, of bandages connected to or including different types of medical sensors or leads. As discussed herein, the term bandage sensor may encompass any combination of a wound covering (e.g. a bandage) and a sensing component that is used to simultaneously cover and examine a wound or area of injury. As may be appreciated, such sensors may be associated with monitoring systems suitable for receiving and processing signals derived from the sensor. By way of illustration, FIG. 1 is a perspective view of an embodiment of a pulse oximetry system 10. The system 10 includes a bandage sensor 12 that includes a bandage 14 with biodegradable waveguides 16 and a pulse oximetry monitor 18. The bandage sensor 12 may include an emitter 20 for emitting light at one or more wavelengths toward a patient's tissue 22 via the biodegradable waveguides 16. In some embodiments, the emitter 24 may be optically connected to the biodegradable waveguides 16 via a fiber optic connector 24. In a similar fashion, a detector 26 may also be provided in the bandage sensor 12 for detecting the light passing through, reflected or fluoresced by the tissue of a patient through the biodegradable waveguides 16. In an embodiment, the detector 26 may be optically coupled to the biodegradable waveguides 16 via a fiber optic connector 28.

In one embodiment, such as where the bandage sensor is wrapped around a finger or toe, light may be transmitted through the measurement site, e.g., an injured area, by regions (e.g., termini of respective biodegradable waveguides 16) of the bandage sensor 12 that are on opposite sides of the site. However, in another embodiment of the bandage sensor 12, the light emitting and detecting regions of the bandage sensor 12 may be arranged so that light is transmitted into and detected from the same side of the measurement site, i.e., a reflectance mode. In such an embodiment, the light may be reflected by the tissue 22 back through a respective biodegradable waveguide 16 and to the detector 26. As discussed, the transmitted and received light may also be transmitted through one or more respective fiber optic connectors 24 and 28 connecting the emitter 20 and detector 26 with respective biodegradable waveguides 16. Further, in one embodiment, the bandage sensor 12 may be electrically and/or optically connected to the monitor 18 as shown. For example, the bandage sensor 12 may be optically coupled to the monitor 18 via cable 30.

The monitor 18 may be configured to calculate physiological parameters based on data received from the bandage sensor 12 relating to light emission and detection. The monitor 18 may include a display 32 configured to display the physiological parameters, other information about the system, and/or alarm indications. In the embodiment shown, the monitor 18 also includes a speaker 34 to provide an audible alarm in the event that the patient's physiological parameters are not within an expected range, as defined based on patient characteristics.

In the illustrated embodiment, the pulse oximetry system 10 also includes a multi-parameter patient monitor 36. The multi-parameter patient monitor 36 may be configured to calculate physiological parameters and to provide a central display 38 for information from the monitor 18 and from other medical monitoring devices or systems. For example, in one embodiment where the monitor 18 is a pulse oximetry monitor, the multi-parameter patient monitor 36 may be configured to display, on the central display 38, a patient's oxygen saturation reading generated by the monitor 18, pulse rate information from the monitor 18, and/or blood pressure from a separate blood pressure monitor. Additionally, the multi-parameter patient monitor 36 may generate a visible or audible alarm via the central display 38 or a speaker 40, respectively, if the patient's physiological characteristics are found to be outside of the expected range. The monitor 18 may be communicatively coupled to the multi-parameter patient monitor 36 via a cable 42 or coupled to a sensor input port or a digital communications port, respectively. In addition, the monitor 18 and/or the multi-parameter patient monitor 36 may be connected to a network to enable the sharing of information with servers or other workstations.

Figure 2:
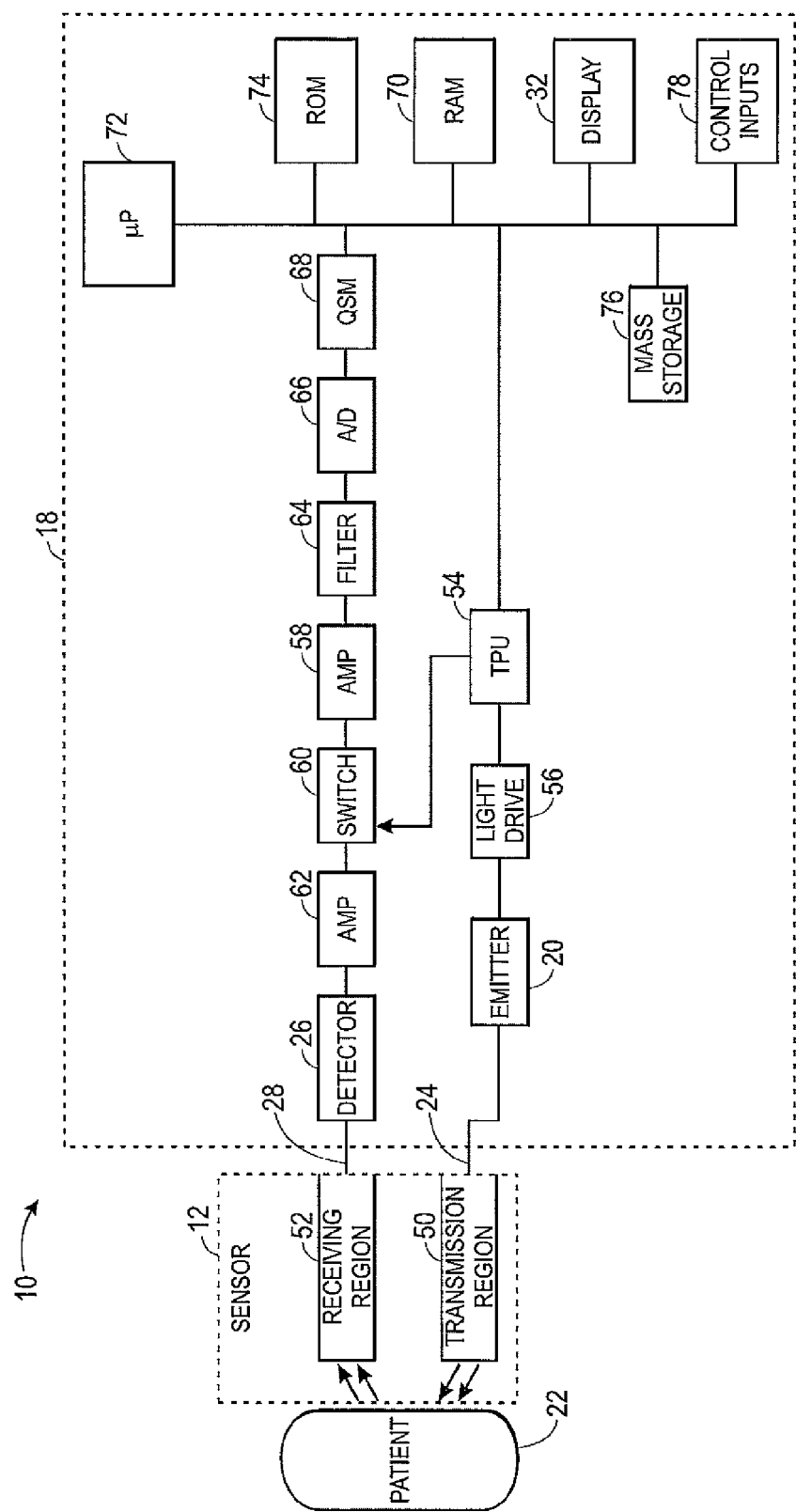
FIG. 2 illustrates a block diagram of a spectrophotometric system, in accordance with various aspects of the present disclosure.

Turning to FIG. 2, the figure depicts a block diagram of an embodiment of the spectrophotometric system 10 that may be configured to implement the techniques described herein. By way of example, embodiments of the system 10 may be implemented with any suitable sensor and patient monitor, such as those available from Nellcor Puritan Bennett LLC. The system 10 may include the patient monitor 18 and the sensor bandage 12 (as discussed with respect to FIG. 1), which may be configured to obtain, for example, a plethysmographic signal from patient tissue at certain predetermined wavelengths.

Bandage sensor 12 may include one or more biodegradable optical fibers or fiber bundles, as discussed herein, in optical communication with the patient monitor 18. Embodiments of the bandage sensor 12 may be free of electronics, metals, and/or other materials that may influence or be influenced by a magnetic field. Additionally, in certain of these embodiments, the bandage sensor 12 may be substantially free of silica, glass and/or other non-biodegradable materials. Certain components of the bandage sensor 12, namely a light transmitting biodegradable waveguide portion 50 (i.e., a biodegradable emitter region) and a light collecting biodegradable waveguide portion 52 (i.e., a biodegradable collector region) are illustrated in FIGS. 4-12 below. Other components of the system 10 include a fiber optic element 24 through which light is transmitted from the monitor 18 to the light transmitting biodegradable waveguide portion 50 and a fiber optic element 28 through which light is transmitted from the light collecting biodegradable waveguide portion 52 to the monitor 18 are also depicted. When the system 10 is in operation, light traveling through the fiber optic element 24 may be emitted by the light emitting biodegradable waveguide portion 50, may pass into the patient tissue 22, may be absorbed and/or scattered by the tissue, and may be collected by the light collecting biodegradable waveguide portion 52 to pass back to the monitor 18 along the fiber optic element 28.

In one embodiment, a time processing unit (TPU) 54 may provide timing control signals to light drive circuitry 56 within the monitor 18. Light drive circuitry 56 may contain a set of emitters (e.g., LEDs, laser diodes, and so forth) which may be capable of emitting light through fiber optic element 24. Light drive circuitry 56 may control which wavelength of light is emitted by turning on a suitable LED configured to emit light near a certain wavelength. Light drive circuitry 56 may also control when light is emitted, and if multiple light sources are used, the multiplexed timing for the different light sources. Light emitted from the light drive circuitry 56 may be transmitted through fiber element or fiber bundle 24 to the sensor 12 and may be transmitted out of the light emitting biodegradable waveguide portion 50 into the patient tissue 22. The light may be absorbed and/or scattered by the tissue, and may be collected by the light collecting terminal portion 52. The light collecting biodegradable waveguide portion 52 may transmit the collected light through the fiber optic element or fiber optic bundles 28 to a detector 26 within the monitor 18. It should be noted that, as shown in FIG. 1, the emitter 20 (and/or light drive 56) and detector 26 may be contained within a separate housing or structure, such that the emitter 20 and detector 26 may be electrically connected to the monitor 18 and optically connected to the bandage sensor 12.

The TPU 54 may also control the gating-in of signals from the detector 26 through an amplifier 58 and a switching circuit 60. These signals may be sampled at the proper time, depending upon which of multiple light sources is illuminated, if multiple light sources are used. In one embodiment, the received signals from the detector 26 may be passed through an amplifier 62, a low pass filter 64, and/or an analog-to-digital converter 66 for amplifying, filtering, and digitizing the received signals. The digital data may then be stored in a queued serial module (QSM) 68, for later downloading to the RAM 70 as the QSM 68 fills up. In an embodiment, there may be multiple parallel paths for separate amplifiers, filters, and A/D converters for multiple light wavelengths or spectra received. This raw digital diagnostic data may be further sampled by the circuitry of the monitor 18 into specific diagnostic data of interest, such as pulse rate, blood oxygen saturation, and so forth.

In various embodiments, based at least in part upon the value of the received signals corresponding to the light detected by detector 26, a microprocessor 72 may calculate a physiological parameter of interest using various algorithms. These algorithms may utilize coefficients, which may be empirically determined, corresponding to, for example, the wavelengths of light used. In one embodiment, these algorithms may be stored in the ROM 74 and/or the mass storage 76.

As depicted, the monitor 18 may include control inputs 78, such as switches, dials, buttons, a keyboard, a mouse, or a trackball, by which a user may interact with the monitor 18. A display 32 of the monitor 18 may be used to show the physiological measurements, alarm limits, and other information of interest to a caregiver. Further, mass storage 76 may store caregiver preferences, patient information, or various parameters, discussed above, which may be used in the operation of the monitor 18. Software for performing the configuration of the monitor 18 and for carrying out the techniques described herein may also be stored on the mass storage 76 and/or on the ROM 74. The mass storage 76 and/or RAM 70 may also store historical values of various discrete medical diagnostic data points. By way of example, the mass storage 76 and/or RAM 70 may store historical or trend values of corresponding to pulse rate, blood oxygen saturation, and total hemoglobin, as well as others.

Figure 3:
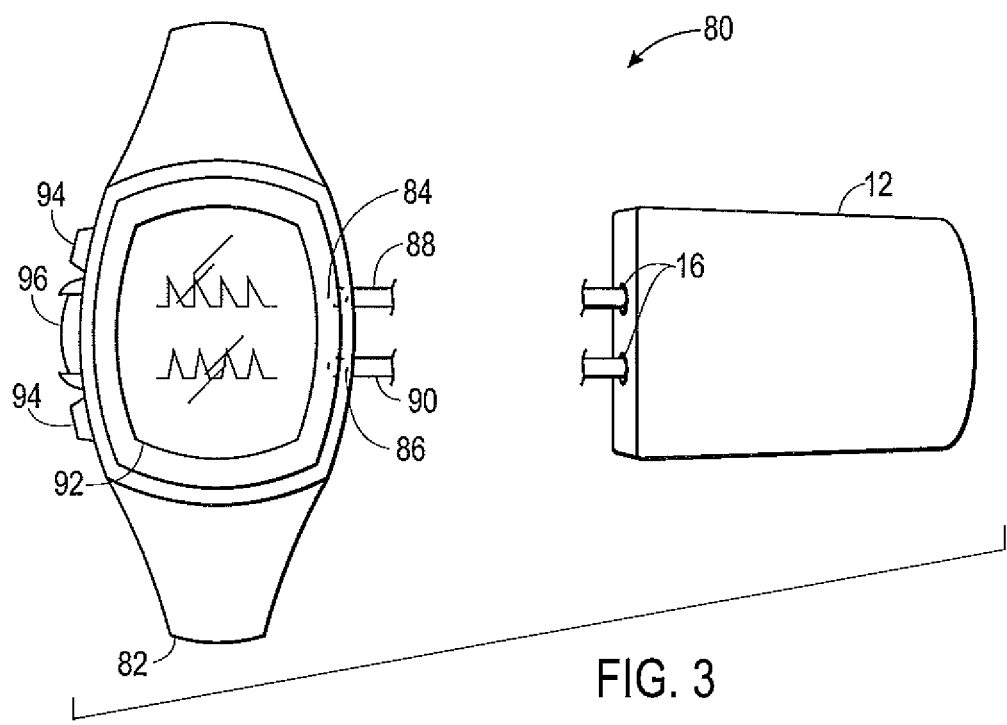
FIG. 3 illustrates a portable monitoring system with an integrated bandage sensor, in accordance with particular aspects of the present disclosure.

While the preceding describes a conventional embodiment such as may be used in a clinical environment, in other embodiments, the bandage sensor 12 may be used in a setting where such conventional monitoring systems may be unavailable. For example, it may be desirable to use the bandage sensor 12 for emergency response, at a remote location, or in a non-clinical setting, such as on a battlefield, at an accident site, or in other emergency contexts. FIG. 3 illustrates an embodiment of a portable system 80 for monitoring an injured patient when traditional healthcare facilities are not readily accessible. The portable system may include a portable device, such as a watch-like device 82 configured to wrap around a portion of a limb (e.g., a wrist). The device 82 may include a built-in emitter 84 and detector 86 that may couple to biodegradable waveguides 16 of the bandage sensor 12 via fiber optic connectors 88 and 90, respectively. As with a conventional monitor system, such as the system 10 illustrated in FIG. 1, the portable monitor system 80 may be configured to calculate physiological parameters based on data received from the bandage sensor 12 relating to light emission and detection. Further, the portable monitor device 82 may include a display 92 configured to display physiological parameters, other information about the system, alarm indications and/or other relevant data. The device 82 may further include multi-function controls 94 such that the device 82 may be configured to monitor any number of patient characteristics and display a desired set of data. The device 82 may further include a communications port 96 to connect and transmit patient data to a number of external monitors and/or storage devices.

As noted above, the bandage sensor 12 may include biodegradable waveguides 16 within a bandage structure 14, which may facilitate the medical examination of an injured area on a patient. The material, shape and extent of the biodegradable waveguides 16 may vary to suit the type or function of bandage sensor 12. That is, the biodegradable waveguides 16 may be formed from different materials that give rise to a number of different optical and physical properties. In addition, the biodegradable waveguides 16 may have dimensions that allow the waveguides 16 to function as single- or multimode optical guides, allowing a variety of light sources to be used as emitters, such as LEDs, broadband lamps, and lasers. The light sources may couple to the biodegradable waveguides 16 via a conventional fiber optic cable or connector, a tapered lens or any similar feature. In one embodiment, the biodegradable waveguides 16 may be provided as a mesh that covers all or most of the patient contacting surface of the bandage sensor 12 or may cover select portions of the bandage sensor 12 (such as patterns, patches, strips, edges, and so forth) that provide sufficient area for analysis, as discussed herein.

Figure 4:
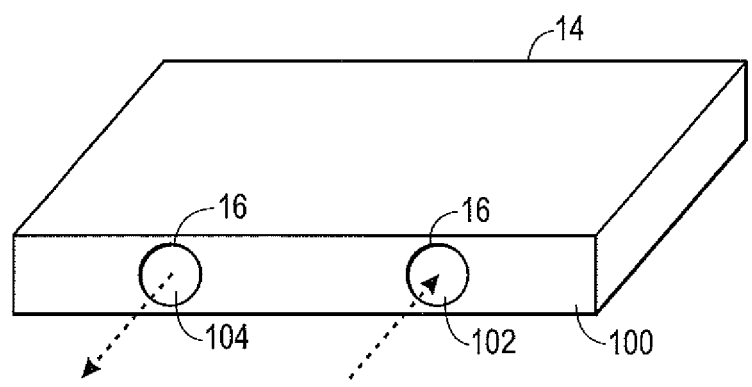
FIG. 4 illustrates a bandage with integrated biodegradable waveguides, in accordance with various aspects of the present disclosure.

FIG. 4 illustrates a bandage structure 14 with biodegradable waveguides 16 disposed within a bandage material 100. In an embodiment, the bandage structure 14 may have two biodegradable waveguides 16, where one respective biodegradable waveguide 102 serves to transmit light to the patient tissue 22, and the other respective biodegradable waveguide 104 serves to transmit light acquired from the patient tissue 22. It may be appreciated that in some embodiments, the bandage sensor 12 may have dedicated areas for light emission and detection. For example, one area of the bandage structure 14 is predominantly or entirely dedicated to light emission, (such as due to placement of the biodegradable emission waveguide 102) while another area of the bandage structure 14 is predominantly or entirely dedicated to light reception, (such as due to placement of the biodegradable reception waveguide 104).

Figure 5:
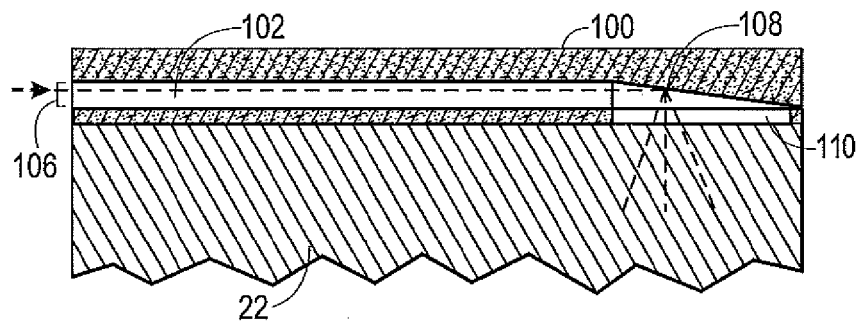
FIG. 5 illustrates a cutaway view of a bandage with integrated biodegradable waveguides for transmission of light to a patient tissue, in accordance with various embodiments of the present disclosure.
Figure 6:
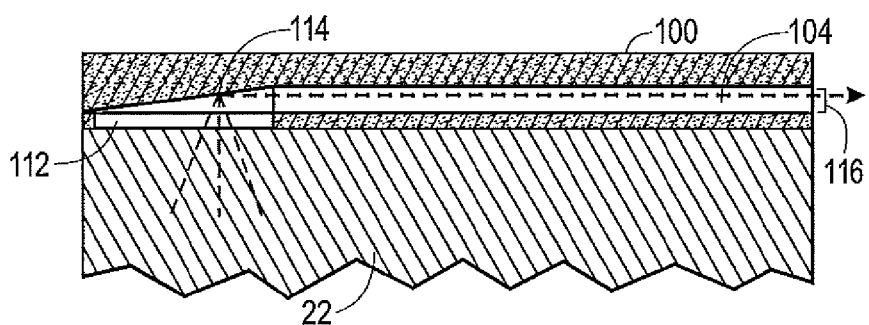
FIG. 6 illustrates a cutaway view of a bandage with integrated biodegradable waveguides for the transmission of light to a detector from patient tissue, in accordance with various aspects of the present disclosure.
Figure 7:
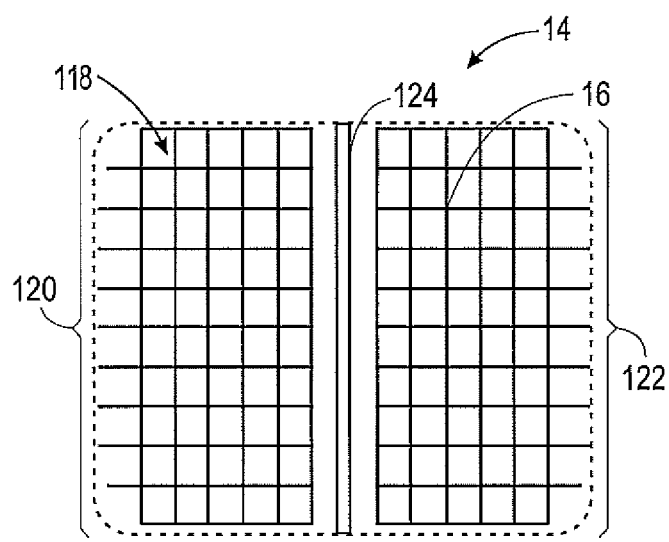
FIG. 7 illustrates a bandage sensor with multiple biodegradable waveguides, in accordance with various aspects of the present disclosure.

In an embodiment, as illustrated in FIGS. 5 and 6, light may enter biodegradable emission waveguide 102 through an aperture 106, propagate down the length of biodegradable waveguide 102 and strike a refraction point 108, which may serve to direct the propagating light through another aperture 110 towards the patient tissue 22. As shown in FIG. 6, the light that has been directed towards the patient tissue 22 may be scattered, transmitted and/or absorbed by the patient tissue 22. The resulting scattered, transmitted and/or fluoresced light emanating from the patient tissue 22 may then enter biodegradable reception waveguide 104 through aperture 112, followed by propagation to refraction point 114, where-upon contacting refraction point 114 the light then is directed down the length of biodegradable waveguide 104 and out through aperture 116 to a photodetector.

While the preceding describes light transmission and reception using separate respective waveguides, in some embodiments these functions may be performed on the same, i.e., a single, biodegradable waveguide 16. For example, the light may be pulsed (as opposed to continuously emitted) to allow the biodegradable waveguide 16 to be substantially free of emitted light at certain intervals. In such an embodiment, the biodegradable waveguide 16 may allow transmission of light in both directions, i.e., toward and away from the patient, with light being transmitted toward the patient during light pulses and with light being transmitted from the patient between light pulses. By way of example, in one embodiment illustrated in FIG. 7, the biodegradable waveguides 16 may be provided as a mesh-like structure 118 on or within the bandage structure 14. In such embodiments, different portions or strands of the mesh-like structure 118 may be associated respectively with light transmission and reception. In other embodiments, the entire mesh-like structure 118 may be used in conjunction with pulsed light transmission such that during light pulses light is transmitted by the mesh-like structure 118 while between light pulses light is received by the mesh-like structure 118.

In some embodiments, the mesh-like structure 118 may allow the observation of a substantial area of the patient tissue 22 covered by the bandage 14. For example, in some aspects, it may be desirable for the waveguides 16 forming the mesh-like structure 118 to deliver light to the patient tissue 22 such that the light that propagates through the fibers exhibits high loss (e.g., >10 dB/m), i.e., the light may leak or escape through the cladding of the biodegradable waveguide 16. In such embodiments, the high loss may be a result of the biodegradable materials, the diameter of the biodegradable waveguide 16, the wavelengths selected, and the like. In some embodiments, the resulting high loss may lead to an increased area of observation. That is, light may travel through the biodegradable material along the length of the waveguides 16, and propagate outward from the waveguide along the way, thereby resulting in a broadened area of patient tissue 22 that is exposed to the emitted light and, therefore, monitored. High loss materials may further allow the collection of scattered, transmitted, and/or fluoresced light from a broader area of the patient tissue 22, i.e., light collection may occur over a greater area as light may enter the waveguide 16 along the length of the waveguide 16 as well as through the terminal portion of the biodegradable waveguide 16.

In some embodiments, the biodegradable waveguides 16 may be formed using a drawing process to form biodegradable microfibers. The process may be performed on specific types of fibers that may, in certain embodiments, allow the formation of complex fiber optic structures, such as multi-core/multi-channel fibers. In other embodiments, the biodegradable waveguides 16 may be formed by micromachining a hydrogel, which may result in single- or multi-mode optical microfibers. The biodegradable waveguides 16 may be weaved or positioned such that the biodegradable waveguides form the mesh-like structure 118. In one embodiment, the biodegradable waveguides 16 may be provided as an optically transmissive structure 120 used for light emission and a separate optically transmissive structure 122 used for light reception. In order that the light emitted from optically transmissive structure 120 does not directly enter into optically transmissive structure 122 without first passing through the tissue 22 of the patient, the optically transmissive structures may be separated by an opaque barrier 124. Additionally, multiple optically transmissive structures may be employed concurrently to sample various areas of the patient tissue 22, such as to ensure that the entire area of injury is represented by the collected data. In such aspects, there may be more than two separate and distinct optically transmissive structures (such as 120, 122) disposed within the same or separate bandages 14 such that there may be multiple sites that light may enter the tissue 22 and multiple sites that light may exit the tissue 22. In such embodiments, it may be appreciated that there may be multiple opaque barriers 124 provided to prevent light shunting, i.e., direct transmission of light from a light emitting structure to a light receiving structure.

Figure 8:
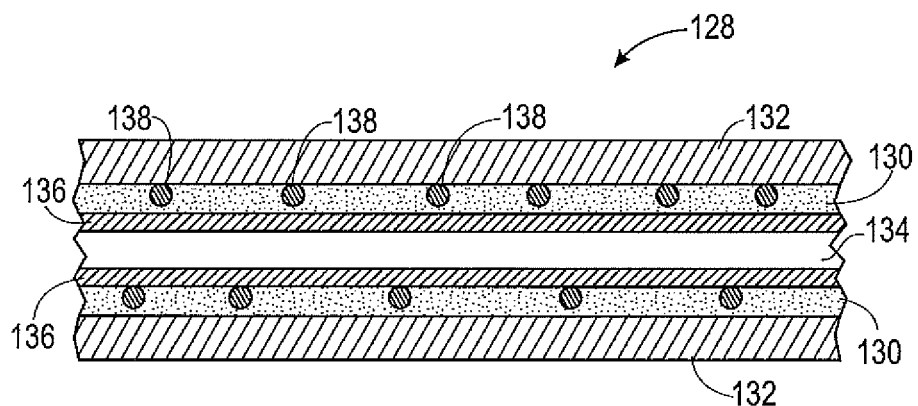
FIG. 8 illustrates a cutaway view of an embodiment of a biodegradable waveguide, in accordance with various aspects of the present disclosure.
Figure 9:
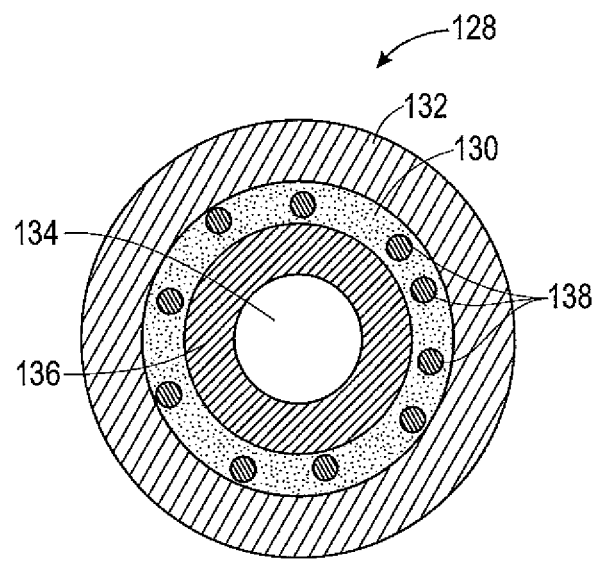
FIG. 9 illustrates an end-on view of an embodiment of a biodegradable waveguide, in accordance with various aspects of the present disclosure.
Figure 10:
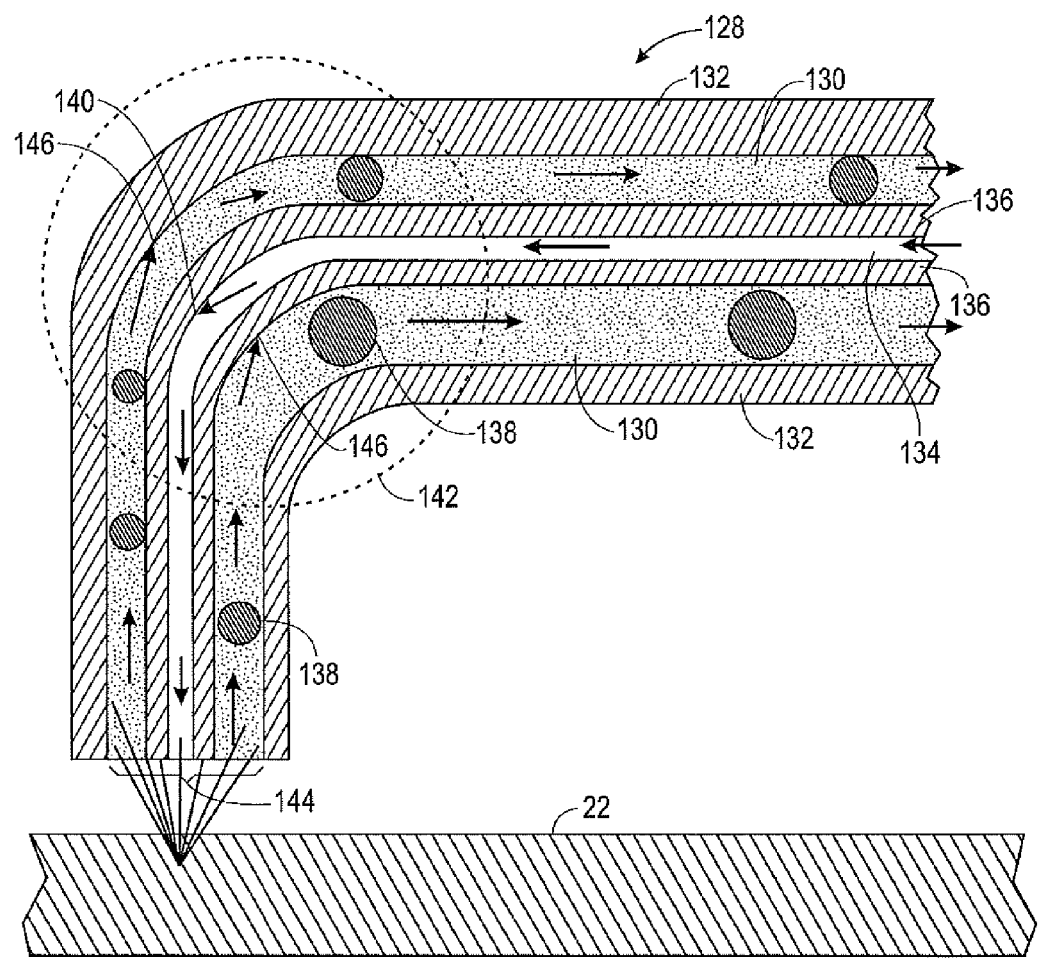
FIG. 10 illustrates a cutaway view of an embodiment of a biodegradable waveguide that can transmit emitted and received light from patient tissue, in accordance with various aspects of the present disclosure.
Figure 11:
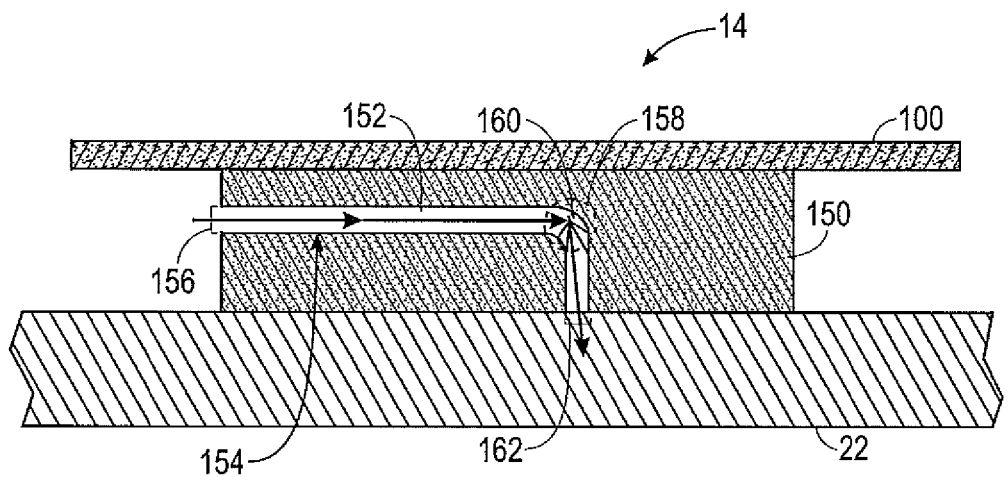
FIG. 11 illustrates a cutaway view of a micromachined hydrogel waveguide serving to transmit light from a light source to a patient tissue.

Moving now to FIGS. 8 through 10, in some embodiments, the biodegradable waveguides 16 may be multi-channel optical fibers, such as dual-channel optical fibers 128. Such fibers may be formed by drawing large diameter fibers and concentric, smaller diameter fibers into microfibers. For example, the diameter of the larger, outer fiber may be between about 1 mm and about 20 cm before drawing, and tens to hundreds of microns ($\mu$m) (e.g., about 10 $\mu$m to about 500 $\mu$m) afterwards. The smaller fibers (the inner fibers) may have initial diameters similar to that of the outer fiber (inasmuch as the inner fibers are able to be placed within the outer fiber). The drawing process may result in inner fibers with diameters in the range of 1 $\mu$m to 50 $\mu$m, resulting in single- or multi-mode optical fibers. The outer fiber may form an outer channel 130 and outer cladding 132 that is spaced from the smaller concentric fibers (that may form an inner channel 134 and an inner cladding 136) by a support material 138 that fills the outer channel 130. When the biodegradable waveguides 16 are formed by such a drawing process, the biodegradable waveguides 16 may exhibit properties resembling single- or multi-mode optical fibers, depending not only on the dimensions of the channels, but on which channel is coupled to the light source. That is, light propagating substantially down the multi-mode outer channel 130 may have varying pathways. Light propagating substantially down the inner channel 134 may or may not have varying pathways, depending on the size of the inner channel 134. Thus, it should be appreciated that, with the foregoing comments in mind, the embodiments described herein may be implemented using multi-channel/multi-core biodegradable fibers, even in instances where dual-channel/dual-core fibers are described to simplify explanation and description.

In the illustrated embodiment in FIG. 9, a dual-channel biodegradable fiber waveguide 128 formed by the process described above includes an outer cladding 132, an outer channel 130, an inner cladding 136 and an inner channel 134 for transmission of light to and from an area of patient tissue 22. The outer and inner claddings may be formed from a biodegradable material, which may be any one or a combination of textiles. For example, textiles including poly (lactic acids), synthetic and natural silks, cellulose and its derivatives, chitin and chitosan derivatives, alignates, sugars, and poly (hydroxyalkanoates) may degrade away after a given amount of time after being disposed on or within a patient. In some embodiments, the cladding material may be selected such that the material is transparent to wavelengths of interest, which may allow light to travel down the claddings as an evanescent wave. For example, in medical diagnostics, low-energy visible and near-IR wavelengths are often used. Thus, transparencies in the range 0.4 $\mu$m<$\lambda$<1.1 $\lambda$m may be desirable (e.g., 0.7 $\mu$m≤$\lambda$≤1.1 $\mu$m). For example, materials such as hydroxypropyl cellulose, poly (methylmethacrylate) and cellulose butyrate may be used to construct the outer cladding 132 and/or the inner cladding 136. In one embodiment, the outer cladding 132 and inner cladding 136 may be formed from cellulose butyrate.

The outer channel 130 may be formed, at least partially, using a material that is capable of supporting the inner cladding 136 while enabling the outer channel 130 to serve as a waveguide. Therefore, in certain embodiments, it may be desirable for the outer channel 130 to be formed from a combination of materials that have refractive indices close to air (i.e. refractive indices close to 1). In related embodiments, the materials may have a refractive index close to a medium (e.g., water, refractive index of about 1.33) that may fill the cores of the biodegradable fiber waveguide 128. In such embodiments, it may be desirable that the light that propagates down the length of the outer channel 130 does not experience significant loss (e.g., <10 dB/m) due to the support material 138 and/or solution. Further, the outer channel 130 may be formed from materials similar to those used in the inner cladding 136 and outer cladding 132. The outer channel 130 may include particles 138 that support the inner cladding 136, for example, polydisperse hydroxypropyl cellulose powder (refractive index 1.337).

It may be appreciated that the size, shape, and extent of the particles 138 may directly affect the waveguiding properties of the dual-channel fiber 128. Thus, in some embodiments, it may be desirable for the support to be relatively stable during the processes used to form the dual channel fiber 128, for example, during the drawing process. In such embodiments, the particles 138 may have a glass transition temperature ($T_g$) higher than that of the fiber materials. In such embodiments, the drawing process may be performed at a temperature higher than the $T_g$ of the fibers, such that the size and shape of the support particles 138 is not substantially affected. Conversely, in some embodiments, it may be desirable to deform the size and shape of the support material 138, in which case materials may be chosen with $T_g$'s similar to or lower than that of the fiber materials.

The inner channel 134 may be formed from the drawing process described above. In some embodiments, an inner fiber with an original (pre-drawing) diameter smaller than that of the original (pre-drawing) diameter of the outer fiber is drawn to a diameter such that the inner channel 134 diameter approaches the dimensions of a single-mode optical fiber (e.g. between 1 μm and 50 μm, or between 8 μm and 10 μm). The exemplary dimensions may allow efficient delivery of light by medically useful laser modalities, such as Nd:YAG, Er:YAG, and $CO_2$, or LED and broadband lamp sources, such as tungsten-halogen lamps.

As can be appreciated in view of the aforementioned material and constructive embodiments, the biodegradable fiber waveguides 128 may be integrated into the bandage sensor 12 to monitor various patient characteristics, as illustrated in FIG. 10. In the illustrated embodiment, a dual-channel biodegradable fiber waveguide 128 is bent to allow light delivery to the patient tissue 22. In other embodiments, the fiber is not bent (i.e., is substantially straight) and delivers the light to a refraction point 140, similar to those described with respect to FIGS. 5 and 6. In other embodiments, an area where the waveguide 128 exhibits a curvature 142 may serve as a refraction point 140 to redirect the transmitted light. In such an embodiment, light emitted from a source, such as a LED, laser or broadband lamp may enter the inner channel 134 by way of a focused lens or laser beam, such that the light propagates down the inner channel 134 in a single-mode fashion. Upon contacting curvature 142 of the inner channel 134, the light may be reflected and/or refracted towards the patient tissue 22 which may scatter, transmit and/or absorb the light.

Upon transmission and/or scattering of the light by the patient tissue 22, the light may enter the outer channel 130, which is larger in diameter compared to the inner channel 134 in the depicted embodiment. In some embodiments, the outer channel 130 may have a larger surface area available for light transmission relative to the inner channel 134, allowing more light to be collected, i.e., increased light sensitivity. Thus, the light emanating from the patient tissue 22 may enter the outer channel 130 through aperture 144 and propagate towards a detector. In the illustrated embodiment, the light may contact refraction point 146 of the outer channel 130 (or the area of curvature 142) and be reflected and/or refracted such that the light propagates down the outer channel 130 and out to a detector. In other embodiments, the biodegradable waveguide 128 may or may not be bent or curve, and may be coupled to a grating and/or light scattering element, such that light emanating from the patient tissue 22 is reflected and/or refracted into aperture 144, propagated down the length of the outer channel 130 and out to a detector.

As previously mentioned, in certain of these embodiments, it may be desirable to surround one or more biodegradable waveguides with a liquid medium, for example, a water or a physiological saline solution, to farm a gel-like structure disposed on the bandage sensor 12. Thus, in such embodiments the support material 138 of the outer channel 130 may be selected to closely match the refractive index of such a liquid medium. For example, water and saline both have refractive indices of about 1.33. As another example, a 10% glucose solution (refractive index of about 1.34) may be used as a source of nutrients to speed recovery of an injured area, or as an alternative inert liquid medium. Thus, the aforementioned support materials 138, for example hydroxylpropyl cellulose (refractive index 1.37), may be chosen to meet a variety of desired properties, including having a refractive index similar to a surrounding medium. As may be appreciated in view of these and other aspects of the embodiments described, as mentioned, the dimensions of the support material 138 may also be varied to tailor the properties of the biodegradable waveguides 128 for a number of applications. For example, in some embodiments the support material 138 may be a monodisperse array of particles of a size consistent with a desired property.

While materials and methods have been described in exemplary embodiments for the construction of dual-channel biodegradable fiber waveguides 128 with two channels, it should be appreciated that similar methods may be used to construct biodegradable waveguides having more than or less than two channels, for example, between 1 and 5 channels. In some embodiments, it may be desirable to construct biodegradable waveguides 16 with a single core. To form regular, tube-like structures that include a biodegradable waveguide 16, a number of materials may be used such that above the $T_g$ of the material, a tube-like structure (a fiber) may be drawn down to dimensions consistent with the particular applications in which the biodegradable waveguide 16 will be used. For example, the materials used may be any one or a combination of textiles and materials including poly(lactic acids), synthetic and natural silks, cellulose and its derivatives, chitin and chitosan derivatives, alignates, sugars, and poly(hydroxyalkanoates). In an embodiment, a hollow glucose tube of outer and inner diameter greater than 1 mm may be drawn at a temperature around about 146° C. to yield a biodegradable waveguide 16 that may be a single- or multi-mode optical microfiber. That is, the tubular glucose microfiber may have outer and inner diameters at or below 500 μm, such as, 500 μm and 50 μm, respectively.

In addition to drawing processes described above, the biodegradable waveguides 16 may be formed by other methods, such as etching, lithography and machining. With these aspects in mind, in some embodiments, the biodegradable waveguides 16 may be formed by a micromachining process performed on a hydrogel. In such embodiments, illustrated in exemplary FIGS. 11 and 12, a bulk hydrogel 150 is disposed on the bandage material 100 of the bandage structure 14. The bulk hydrogel 150 may be formed by maintaining a polymer that is able to absorb a substantial amount of its weight in water in an aqueous solution, such as a physiological saline solution. By way of example, the polymer chosen to form the bulk hydrogel 150 may be able to absorb between 30% and 80% water by weight.

The bulk hydrogel 150 may also be selected such that the material exhibits nonlinear optical behavior (NLO behavior). Such NLO behavior may allow a laser, of properly selected power, wavelength, repetition rate and focal diameter to machine hydrogel waveguides 152 into the bulk hydrogel 150. Typically, materials that exhibit NLO behavior may have chemical functionalities that undergo a polarization change after absorbing a photon. For example, the polymer of the bulk hydrogel 150 may be any one or a combination of polymers that are unsaturated hydrocarbon derivatives, or that have a functionality that absorbs at the wavelength or wavelengths of interest and undergo a change in polarization as a result. By way of example, the polymers may be silicone-containing, acrylate derivatives, and/or vinyl arenes (e.g., poly(2-hydroxyethyl methacrylate) or copoly(2-hydroxyethyl methacrylate-N-1-vinyl-2-pyrrolidinone)). In one embodiment, the NLO properties of the hydrogel 150 may allow a laser, using correctly selected parameters, to induce local changes in the refractive index of the bulk hydrogel 150 material.

For example, due to the nonlinear absorption of photons by the bulk hydrogel 150 material, a laser with a low repetition rate (e.g. between 10 Hz and 1 MHz), focused on a section (e.g., between 1 μm$^3$ and 10 μm$^3$) of hydrogel and with power ranging from microjoules to millijoules may induce a change in the material with every irradiative pulse that is performed in a section confined to the focal volume. Thus, moving the hydrogel 150 with respect to the fixed laser focal point may result in formation of a three-dimensional single-mode fiber optic structure (diameter in the range of 1 μm to 10 μm) with an asymmetric modification profile (areas of different refractive indices). As the focal area disperses its thermal energy in the time between each irradiative pulse, the change in the hydrogel 150 material may be associated with the absorption of photons. Conversely, at higher repetition rates (>1 MHz) coupled with lower laser power on the order of nano joules, the thermal energy resulting from irradiation has a cumulative effect, as the thermal energy may not be able to completely diffuse in the time between each irradiative pulse. Such localized heating may cause a volume slightly larger than the focal volume, such as a section with diameter of 2 μm to 5 μm, to be affected.

Therefore, the factors responsible for the change in the refractive index of the bulk hydrogel 150 material may not be attributed to each respective pulse, but rather to an accumulation of laser pulses and the corresponding cumulated thermal energy. This may result in single-mode fiber optic structures with symmetric modification profiles (symmetrical distribution of refraction indices), as may be desirable with some waveguide applications. However, it may be appreciated that asymmetric changes in the refractive index of the bulk hydrogel material may also have benefits in certain of these embodiments as described herein. With the foregoing comments in mind, in some embodiments, it may be desirable to machine the bulk hydrogel material with high repetition, low power laser irradiation to form a hydrogel waveguide 152 with a symmetric refractive index. In other embodiments, it may be desirable to machine the bulk hydrogel 150 material with low repetition, high power laser irradiation to form a hydrogel waveguide 152 with an asymmetric refractive index. In further embodiments, it may be desirable to machine the bulk hydrogel 150 material using high repetition, low power laser irradiation to form certain sections of a hydrogel waveguide 152 and using low repetition, high power laser irradiation to form other sections of the hydrogel waveguide 152 such that the resulting hydrogel waveguide 152 has areas of symmetric and areas of asymmetric refractive indices.

Returning to FIGS. 11 and 12, the bulk hydrogel 150, having been micromachined to form hydrogel waveguides 152, may exhibit a different refractive index than the hydrogel waveguide-bulk hydrogel interface 154. As a result of this refractive index differential, upon introduction of emitted light into aperture 156, a substantial amount of the light may remain confined within the hydrogel waveguide 152 as the light propagates towards the patient tissue 22. In one embodiment, as the propagating light reaches a curvature 158 in the hydrogel waveguide 152, the light may contact an optional wavelength-selective element 160, such as a diffraction grating, a prism, and/or a lens. In an embodiment, during manufacture of the hydrogel waveguide 152 the laser power and scan rate may be adjusted such that the micromachining process is carried out at a low repetition, high power setting, resulting in a waveguide area that is relatively rough in morphology. Such a rough area may serve as the wavelength-selective element 160 to disperse and refract only certain wavelengths of light towards the patient tissue 22. The propagating light, having contacted the curvature 158 of the waveguide (and in some embodiments, the wavelength-selective element 160) may then be directed towards the patient tissue 22 through aperture 162.

Figure 12:
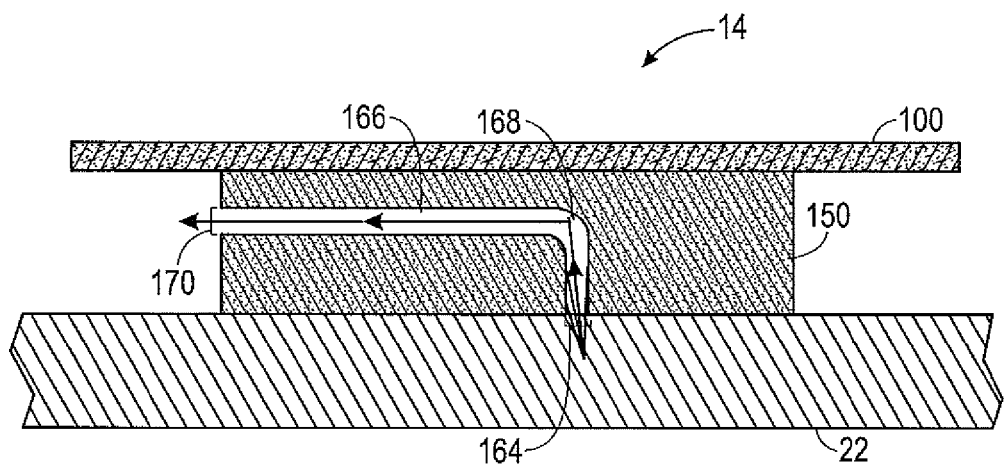
FIG. 12 illustrates a cutaway view of a micromachined hydrogel waveguide serving to transmit light from a patient tissue to a detector or monitor.

As illustrated in FIG. 12, upon contacting the patient tissue 22, the light may be scattered, transmitted and/or absorbed and fluoresced to be collected at an aperture 164 of a hydrogel waveguide 166. In certain embodiments, the second hydrogel waveguide 166 may be disposed on an opposite side of the bandage sensor 12 from the hydrogel waveguides 152 used for emitting, though in other embodiments the emitting hydrogel waveguide 152 and the receiving hydrogel waveguide 166 may be provided on the same side of the tissue site. In some embodiments, an opaque barrier, such as the opaque barrier 124 of FIG. 7, may serve to optically isolate an emission side from a detection side of the bandage sensor 12 to prevent shunting of light. To allow efficient collection of the scattered, transmitted and/or fluoresced light, hydrogel waveguide 166 may be machined in such a way as to form a high numerical aperture multi-mode optical fiber. Such multi-mode hydrogel waveguides may have diameters greater than 10 μm, for example, between 20 μm to 50 μm. Upon collection into hydrogel waveguide 166, the light emanating from the patient tissue 22 may, in one embodiment, propagate to a wavelength-selective element 168, such that the selected wavelengths of light may be focused or dispersed down the length of hydrogel waveguide 166, through an aperture 170, and out towards a detector. Indeed, in some embodiments, as described with respect to FIGS. 4-6, in which the light source is pulsed, a single hydrogel waveguide may function as both the emitting and receiving waveguide.

As may be appreciated with respect to the materials and methods used to construct hydrogel waveguides 152, 166, it may be desirable to include features used to deliver therapeutics to the injured patient tissue 22 at the sensor site. Therefore, in some embodiments, the bulk hydrogel 150 may be doped or treated with any one or a combination of antibiotics, pain relievers, growth factors, healing agents, antivirals, or any therapeutic compound that does not significantly affect the optical performance of the hydrogel waveguides 152, 166. In some embodiments, the bulk hydrogel material 150 may itself display antimicrobial properties. In other embodiments, the therapeutics may be delivered to the patient tissue 22 directly through the hydrogel waveguides 152, 166, such that the performance of the hydrogel waveguides 152, 166 is not significantly affected after elution. The therapeutics may elute through the bulk hydrogel 150 or through the hydrogel waveguides 152, 166 over a given period of time (e.g., between 2 hours and 2 days), during which the hydrogel waveguides 152, 166, in concert with the bandage sensor 12, may serve to provide feedback concerning the injured area. In other embodiments, it may be desirable to continuously monitor the patient tissue 22 as the therapeutics elute through the hydrogel waveguides 152, 166.

In some embodiments, the feedback gained from monitoring the patient tissue 22 via the hydrogel waveguides 152, 166 may be affected by the presence of such therapeutics. As such, correction factors may be introduced to account for a known concentration of therapeutics within the bandage sensor 12, optically transmissive structure 120 and/or 122, bulk hydrogel 150, and/or hydrogel waveguides 152, 166. The feedback may be in the form of scattered, transmitted and/or fluoresced light that may have distinct signatures characteristic of any one or a combination of infection, the presence of foreign bodies, the health of the injured area and/or indications of when the bandage should be changed.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may be applied to measurements of blood oxygen saturation as well as other physiological measurements. Rather, the various embodiments may cover all modifications, equivalents, and alternatives falling within the spirit and scope of the disclosure as defined by the following appended claims.

What is claimed is:

1. A spectrophotometric system, comprising:
a physiological monitor configured to measure one or more physiological parameters of a patient; and
a physiological sensor configured to communicate with the monitor, the physiological sensor comprising:
a light emitting region comprising one or more fibers capable of emitting light along their respective lengths; and
a light receiving region comprising one or more fibers capable of receiving light along their respective lengths; and
wherein the one or more fibers capable of emitting light and the one or more fibers capable of receiving light are configured to degrade after being disposed on or within the patient.

2. The spectrophotometric system of claim 1, wherein the one or more fibers capable of emitting light and the one or more fibers capable of receiving light comprise multi-channel/multi-core optical microfibers.

3. The spectrophotometric system of claim 1, wherein the one or more fibers capable of emitting light and the one or more fibers capable of receiving light comprise hydrogel waveguides.

4. The spectrophotometric system of claim 1, wherein the one or more fibers capable of emitting light along their respective lengths comprise the one or more fibers capable of receiving light along their respective lengths.

5. The spectrophotometric system of claim 1, wherein the physiological monitor comprises a pulse oximetry monitor or a multi-parameter monitor.

6. The system of claim 1, wherein the one or more fibers capable of emitting light, the one or more fibers capable of receiving light, or a combination thereof, are provided as a mesh.

7. The system of claim 6, wherein the mesh is configured to exhibit a loss greater than 10 dB/m.

8. The system of claim 1, wherein the one or more fibers capable of emitting light and the one or more fibers capable of receiving light each comprise at least a first optical channel and a second optical channel disposed concentrically about the first optical channel, the first optical channel has a diameter of between about 1 micrometer and 50 micrometers, and the second optical channel has a diameter of between about 10 micrometers and 500 micrometers.

9. The system of claim 1, wherein the one or more fibers capable of emitting light and the one or more fibers capable of receiving light comprise a cladding comprising hydroxypropyl cellulose, cellulose butyrate, or a combination thereof.

10. The system of claim 1, comprising a cable communicatively coupling the physiological monitor and the physiological sensor.

11. The system of claim 1, wherein the physiological monitor comprises:
an emitter configured to transmit the light through the one or more fibers capable of emitting light; and
a detector configured to receive the emitted light via the one or more fibers capable of receiving light.

12. The system of claim 1, wherein the physiological sensor comprises an opaque barrier positioned between the light emitting region and the light receiving region.

13. A physiological sensor configured to communicate with a physiological monitor to monitor one or more physiological parameters of a patient, the physiological sensor comprising:
a light emitting region comprising one or more fibers capable of emitting light along their respective lengths; and
a light receiving region comprising one or more fibers capable of receiving light along their respective lengths; and
wherein the one or more fibers capable of emitting light and the one or more fibers capable of receiving light are configured to degrade after being disposed on or within the patient.

14. The physiological sensor of claim 13, wherein the one or more fibers capable of emitting light and the one or more fibers capable of receiving light comprise multi-channel/multi-core optical microfibers.

15. The physiological sensor of claim 14, wherein a cladding of the multi-channel/multi-core optical microfibers comprises hydroxypropyl cellulose, cellulose butyrate, or a combination thereof.

16. The physiological sensor of claim 15, wherein the cladding is transparent to the emitted light.

17. The physiological sensor of claim 14, wherein a channel of the multi-channel/multi-core optical microfibers comprises polydisperse hydroxypropyl cellulose powder.

18. The physiological sensor of claim 13, wherein the one or more fibers capable of emitting light and the one or more fibers capable of receiving light comprise hydrogel waveguides.

19. The physiological sensor of claim 13, comprising:
- an emitter configured to transmit one or more wavelengths of light, wherein the emitter is spaced apart from a body of the physiological sensor and is optically coupled to the one or more fibers capable of emitting light;
- a photodetector configured to receive the emitted light, wherein the detector is spaced apart from the body of the physiological sensor and is optically coupled to the one or more fibers capable of receiving light.

20. A spectrophotometric system, comprising:
- a physiological monitor configured to measure one or more physiological parameters of a patient;
- an emitter communicatively coupled to the physiological monitor and configured to emit one or more wavelengths of light;
- a detector communicatively coupled to the physiological monitor and configured to detect the light emitted by the emitter; and
- a physiological sensor configured to communicate with the physiological monitor, the physiological sensor comprising:
  - a light emitting region optically coupled to the emitter and comprising one or more first fibers capable of transmitting the light emitted by the emitter along their respective lengths toward a patient tissue; and
  - a light receiving region comprising one or more second fibers capable of receiving the light emitted by the emitter, wherein the one or more second fibers are configured to transmit the received light to the detector; and
  - wherein the one or more first and the one or more second fibers are configured to degrade after being disposed on or within the patient.

* * * * *